United States Patent
Collazo (10) Patent No.: US 6,896,702 B2
(45) Date of Patent: May 24, 2005

(54) SECURING AN AUGMENT TO A PROSTHETIC IMPLANT COMPONENT

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 25 days.

(21) Appl. No.: 10/143,738

(22) Filed: May 10, 2002

(65) Prior Publication Data

US 2004/0030397 A1 Feb. 12, 2004

(51) Int. Cl.[7] .................................................. A61F 2/38
(52) U.S. Cl. .................................. 623/20.16; 623/20.32
(58) Field of Search .......................... 623/20.32, 20.14, 623/20.16, 20.33–20.34

(56) References Cited

U.S. PATENT DOCUMENTS

| | | |
|---|---|---|
| 4,944,757 A | 7/1990 | Martinez et al. |
| 5,019,103 A | 5/1991 | Van Zile et al. |
| 5,152,797 A | 10/1992 | Luckman et al. |
| 5,344,461 A | 9/1994 | Phlipot |
| 5,458,637 A | 10/1995 | Hayes |
| 5,928,286 A * | 7/1999 | Ashby et al. ............ 623/20.33 |
| 6,039,764 A | 3/2000 | Pottenger et al. |

FOREIGN PATENT DOCUMENTS

| | | |
|---|---|---|
| EP | 0 336 774 | 10/1989 |
| EP | 0 538 987 | 4/1993 |

* cited by examiner

*Primary Examiner*—Thomas Barrett
(74) *Attorney, Agent, or Firm*—Arthur Jacob (57) ABSTRACT

A selected augment, shown as a tibial augment, is secured at an augmentation location on a prosthetic implant component, shown as a tibial implant component, by a securing element assembled with the body of the augment for displacement relative to the augment body to selectively engage an abutment located on a depending structure of the implant component, adjacent the augmentation location, so as to establish a securing force between the securing element and the depending structure for urging the augment against the implant component, and thereby secure the augment to the implant component at the augmentation location. In the tibial augment, a distal surface includes surface portions extending in anterior-posterior directions and oriented essentially normal to medial-lateral directions.

24 Claims, 5 Drawing Sheets

SECURING AN AUGMENT TO A PROSTHETIC IMPLANT COMPONENT

BACKGROUND OF THE INVENTION

1. Field of the Invention

The present invention relates generally to prosthetic implants and pertains, more specifically, to a construction and a method for facilitating securement of a selected augment to an implant component, such as the securement of a selected tibial augment to a tibial implant component of a prosthetic knee implant.

2. Description of Related Art

In a knee implant procedure, for example, very often tibial augments, or spacers, are employed by a surgeon to compensate for a bone defect encountered at the implant site. Typically, a tibial augment is selected during the course of surgery, upon observation of the actual implant site, and is attached by the surgeon to the lower, or distal surface of the tibial tray of a tibial implant component utilizing attachment screws, bone cement, or a combination of screws and cement. Both screws and cement exhibit certain drawbacks.

Thus, where bone cement is used to attach a tibial augment to the tibial tray, the cement ordinarily is mixed during surgery and is placed between the augment and the tibial tray. The tibial augment then is secured in place with a clamp and is held in place until the cement cures. Unwanted delay is experienced as a result of the requirement for waiting until the cement cures before going forward with the implant procedure. In addition, the extra steps involved in mixing the cement, applying the cement, and then clamping the augment to the tibial tray require added effort as well as increased time, all to the detriment of both the patient and the surgeon.

The use of attachment screws requires the mechanical assembly of a selected tibial augment with the tibial tray of a tibial implant component, again during surgery. The tibial tray is provided with apertures passing entirely through the tibial tray, and the tibial augment includes holes in locations corresponding to the apertures in the tibial tray. In executing the assembly, screws either are inserted through unthreaded apertures in the tibial tray and then threaded into corresponding threaded holes in the tibial augment to secure the augment against the distal surface of the tibial tray, or the screws are passed through unthreaded holes in the augment to be threaded into threaded apertures in the tibial tray to secure the augment in place. In either procedure, the surgeon must contend with handling small loose screws and threading the screws into place. In addition, apertures in the tibial tray can allow particulate polyethylene debris from a bearing member supported at the proximal surface of the tibial tray to migrate through the tibial tray and into the adjacent bone during service of the implant, causing deleterious effects. Further, the presence of apertures in the tibial tray reduces the area of the proximal surface available for support of the bearing member, thereby increasing stress on the material of the bearing member and encouraging cold flow of polyethylene into the apertures of the tibial tray, with concomitant distortion of the bearing member.

BRIEF SUMMARY OF THE INVENTION

The present improvement provides a construction and method which facilitates the securement of a selected augment to an implant component, such as the securement of a selected tibial augment to a tibial implant component, while avoiding the drawbacks outlined above. As such, the present improvement attains several objects and advantages, some of which are summarized as follows: Enables a, surgeon quickly and effectively to attach a selected augment to an implant component, such as the attachment of a selected tibial augment to a tibial implant component, interoperatively, without resorting to cementing and clamping, as described above, and without the necessity for assembling loose fasteners with the augment and the implant component; avoids deleterious effects which otherwise could result from migrating particulate polyethylene, as described above, as well as cold flow of polyethylene due to excessive stress at surfaces where the bearing member of a tibial implant is supported by the tibial tray of a tibial implant component; provides a self-contained augment in which a securement mechanism is assembled in the factory as a part of the augment for ready use by a surgeon without the necessity for further assembly of augment component parts during the implant procedure; simplifies the selection and placement of an appropriate augment at an implant site without undue delay, thereby benefitting the recipient of a prosthetic implant, as well as assisting the surgeon; provides a simple and highly effective securement arrangement for securing an augment, such as a tibial augment to a tibial implant component without the necessity for special instruments, tools or unusual skills; promotes accuracy and effectiveness in completing a prosthetic implant procedure; enhances the performance and longevity of a prosthetic knee implant which requires the use of a tibial augment; provides a relatively rugged implant assembly capable of exemplary performance over an extended service life.

The above objects and advantages, as well as further objects and advantages, are attained by the present invention which may be described briefly as an improvement for facilitating securement of a selected tibial augment at an augmentation location on a tibial implant component, the tibial implant component having a tibial tray adjacent the augmentation location and a depending structure extending longitudinally from the tibial tray, the tibial tray having a proximal surface and an opposite distal surface, the improvement comprising: an abutment on the depending structure, the abutment extending transversely along the depending structure adjacent the augmentation location; a securing element coupled with the tibial augment for selective rotation about a longitudinal axis of rotation located adjacent the abutment when the tibial augment is placed at the augmentation location and juxtaposed with the tibial tray; and a securing surface on the securing element arranged for longitudinal displacement relative to the abutment upon rotation of the securing element, the longitudinal displacement engaging the securing surface with the abutment to establish a longitudinal securing force between the securing element and the depending structure for urging the tibial augment against the tibial implant component, and thereby secure the tibial augment to the tibial implant component at the augmentation location.

In addition, the present invention includes a method for facilitating selective securement of a tibial augment at an augmentation location on a tibial implant component, the tibial implant component having a tibial tray adjacent the augmentation location and a depending structure extending longitudinally from the tibial tray, the tibial tray having a proximal surface and an opposite distal surface, the method comprising: providing an abutment on the depending structure, the abutment extending transversely along the depending structure adjacent the augmentation location; coupling a securing element with the tibial augment for selective rotation about a longitudinal axis of rotation located adjacent the abutment when the tibial augment is placed at the augmentation location and juxtaposed with the tibial tray; providing a securing surface on the securing element; and rotating the securing element to displace the securing surface longitudinally relative to the abutment, the longitudinal displacement engaging the securing surface with the abutment to establish a longitudinal securing force between the securing element and the depending structure for urging the tibial augment against the tibial implant component, and thereby secure the tibial augment to the tibial implant component at the augmentation location.

Further, the present invention includes an improvement for facilitating securement of a selected augment at an augmentation location on a prosthetic implant component, the improvement comprising: an augment body; an abutment on one of the augment body and the prosthetic implant component, the abutment extending in a first direction along the one of the augment body and the prosthetic implant component, adjacent the augmentation location; a securing element coupled with the other of the augment body and the prosthetic implant component for selective rotation about an axis of rotation extending in a second direction transverse to the first direction and located adjacent the abutment when the augment is placed at the augmentation location and juxtaposed with the prosthetic implant component; and a securing surface on the securing element arranged for displacement in the second direction, relative to the augment body, upon rotation of the securing element about the axis of rotation, the displacement engaging the securing surface with the abutment to establish a securing force in the second direction, between the securing element and the abutment for urging the augment against the prosthetic implant component, and thereby secure the augment to the prosthetic implant component at the augmentation location.

Still further, the present invention includes a method for facilitating securement of a selected augment at an augmentation location on a prosthetic implant component, the method comprising: providing an abutment on one of the augment and the prosthetic implant component, the abutment extending in a first direction along the one of the augment and the prosthetic implant component, adjacent the augmentation location; coupling a securing element with the other of the augment and the prosthetic implant component for selective rotation about an axis of rotation extending in a second direction transverse to the first direction and located adjacent the abutment when the augment is placed at the augmentation location and juxtaposed with the prosthetic implant component; and rotating a securing surface on the securing element to displace the securing surface in the second direction, relative to the augment, upon rotation of the securing element about the axis of rotation, the displacement engaging the securing surface with the abutment to establish a securing force in the second direction, between the securing element and the abutment for urging the augment against the prosthetic implant component, and thereby secure the augment to the prosthetic implant component at the augmentation location.

BRIEF DESCRIPTION OF THE SEVERAL VIEWS OF THE DRAWING

The invention will be understood more fully, while still further objects and advantages will become apparent, in the following detailed description of preferred embodiments of the invention illustrated in the accompanying drawing, in which.

DETAILED DESCRIPTION OF THE INVENTION

Figure 1:
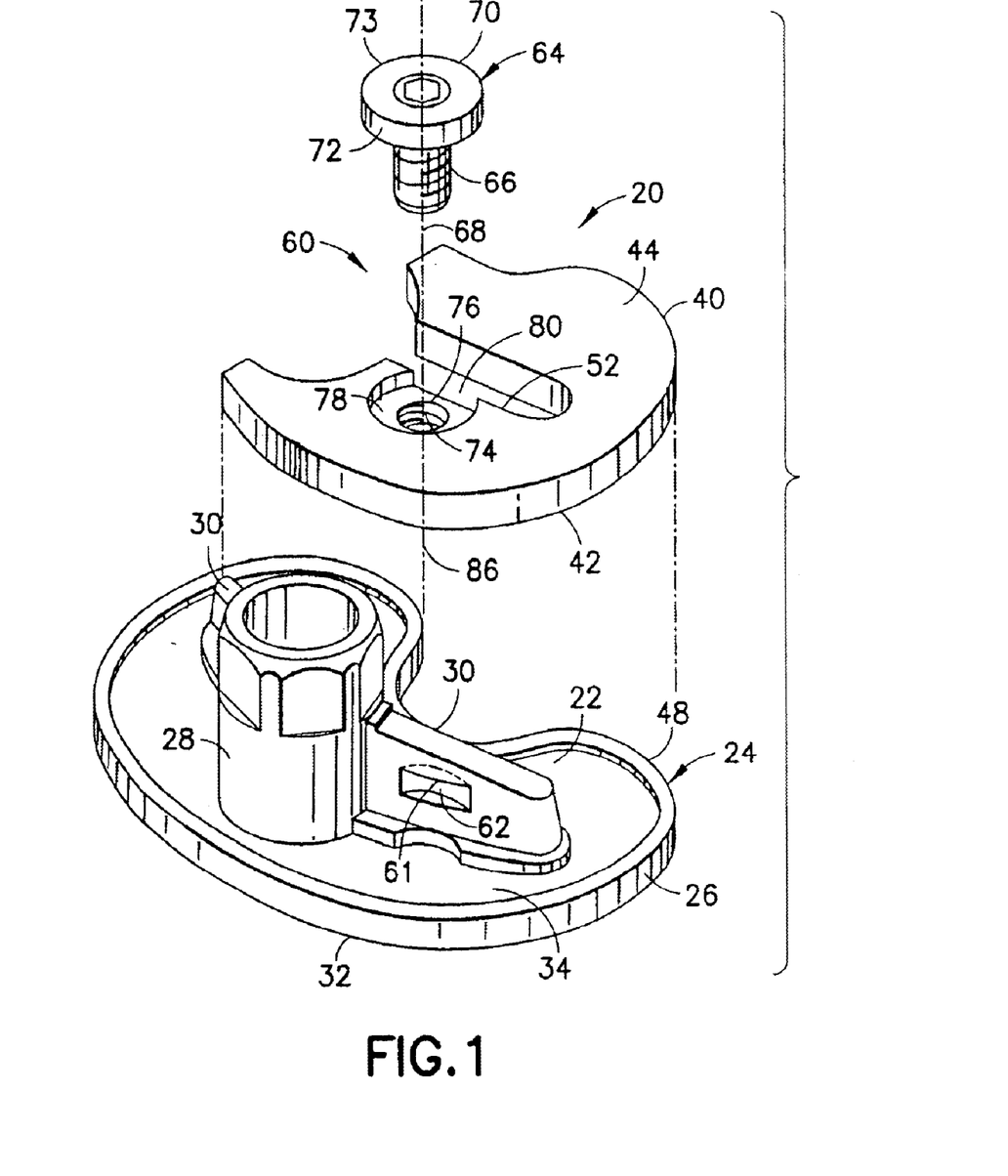
FIG. 1 is an exploded perspective view of a tibial augment and tibial implant component constructed in accordance with the present invention, taken from a distal aspect.

Referring now to the drawing, and especially to FIG. 1 thereof, an improvement in accordance with the present invention is illustrated in the form of a tibial augment 20 to be secured at an augmentation location 22 on a tibial implant component 24. Tibial implant component 24 is constructed in a now-conventional configuration insofar as tibial implant component 24 includes a laterally extending tibial tray 26 and a depending structure, shown in the form of a longitudinally extending stem boss 28, for receiving a stem (not shown) of a complete tibial implant (not shown) and a stabilizing keel 30 which also extends in a longitudinal direction. As is well-known in the construction of tibial implants, tibial tray 26 has a superior, or proximal surface 32 for supporting a bearing member (not shown), usually constructed of a synthetic polymeric material, such as a high density polyethylene, and an inferior, or distal surface 34 for confronting the natural bone of the tibia (not shown) at an implant site.

Depending upon the particular conditions encountered at an implant site, a surgeon may decide to place a tibial augment between the tibial tray of a tibial implant and the confronting natural bone of the tibia to compensate for such conditions. Attachment of the tibial augment to the tibial implant component usually is accomplished during the implant procedure, that is, interoperatively, when the conditions at the implant site can be observed directly and evaluated by the surgeon for appropriate compensation. Thus, a variety of tibial augment constructions have been made available, incorporating a number of different mechanisms for securement of a selected tibial augment to a tibial implant component.

Figure 2:
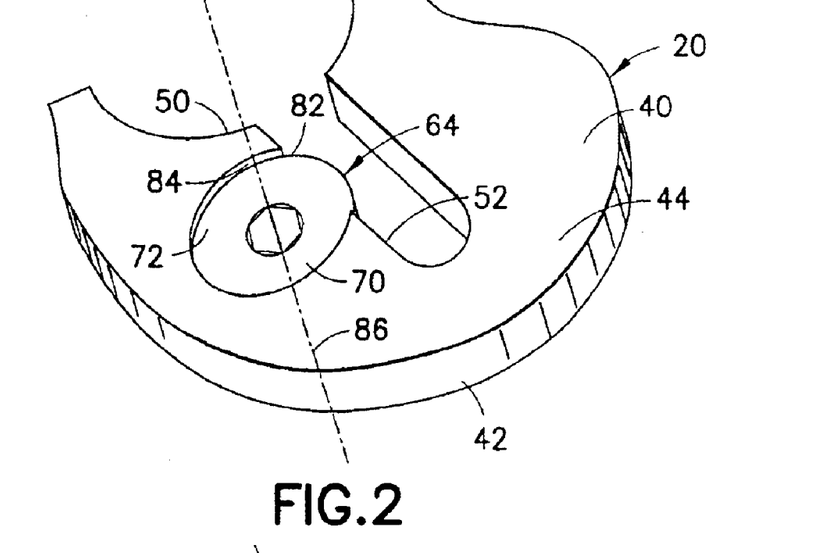
FIG. 2 is a perspective view of the tibial augment taken from a distal aspect.
Figure 3:
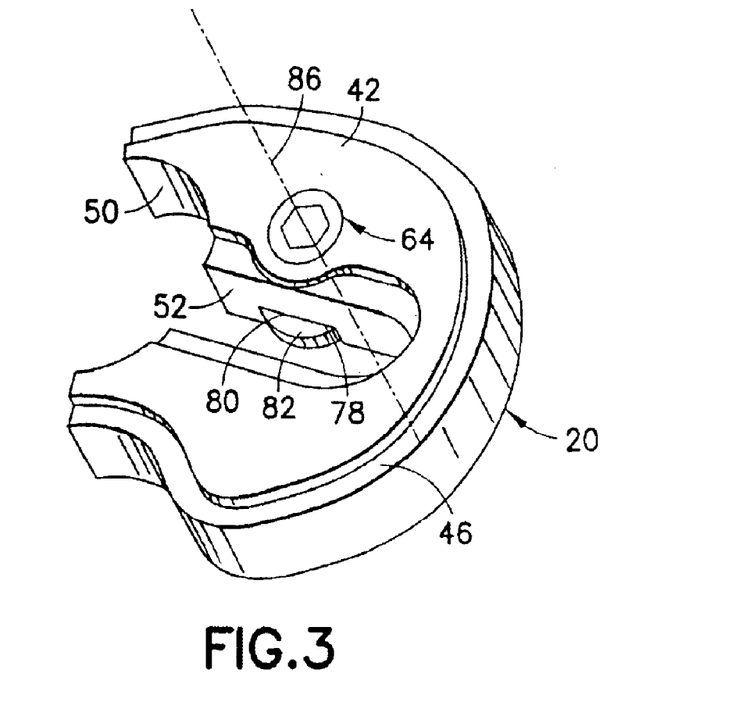
FIG. 3 is a perspective view of the tibial augment taken from a proximal aspect.

Turning now to FIGS. 2 and 3, as well as to FIG. 1, in the illustrated embodiment, tibial augment 20 has been selected for securement to the tibial implant component 24, beneath tibial tray 26, at augmentation location 22. Tibial augment 20 has a body 40 which includes a superior, or proximal surface 42 for confronting the distal surface 34 of the tibial tray 26, and an inferior, or distal surface 44 for engaging the natural bone of the tibia at the implant site. Proximal surface 42 of tibial augment 20 and distal surface 34 of tibial tray 26 essentially are complementary to enable appropriate location and seating of the tibial augment 20 at the augmentation location 22. To that end, the peripheral configuration of tibial augment 20 includes an outer peripheral undercut 46 which essentially follows a corresponding peripheral rim 48 of the tibial tray 26 such that upon seating of the tibial augment 20 at the augmentation location 22, the rim 48 is engaged with the undercut 46 for appropriate location of the tibial augment 20 on the tibial implant component 24. An inner peripheral edge 50 follows a generally circular pattern for providing clearance for the stem boss 28, and a somewhat rectangular opening 52 provides clearance for keel 30, upon proper seating of the tibial augment 20 at the augmentation location 22.

A securing mechanism 60 is provided for securing the tibial augment 20 to the tibial implant component 24 when the tibial augment 20 is appropriately located and seated at the augmentation location 22. In the illustrated embodiment, securing mechanism 60 includes an abutment extending transversely along the tibial implant component 24, the abutment being shown in the form a transverse wall 61 of a slot 62 extending in a first direction, transversely into the keel 30, adjacent the augmentation location 22, and a securing element coupled to the tibial augment 20, the securing element being shown in the form of a threaded member 64 having a helical thread 66, adjacent one end 68 of the threaded member 64, and a generally cylindrical head 70 having a securing surface in the form of a locking surface 72 at the other end 73 of the threaded member 64.

In the position illustrated in FIGS. 2 and 3, the threaded member 64 is in a first, or unlocked position wherein the helical thread 66 is engaged with a complementary helical thread 74 in a threaded hole 76 in the tibial augment 20 and the head 70 is seated within a complementary counterbore 78 coaxial with the threaded hole 76. The counterbore 78 intercepts the opening 52 at 80 so that a portion 82 of the head 70 extends transversely beyond the counterbore 78 and into the opening 52. In the unlocked position of the threaded member 64, as illustrated in FIGS. 2 and 3, the locking surface 72 of head 70 preferably is recessed slightly from the distal surface 44 of the tibial augment 20, as illustrated at 84. The threaded member 64 is coupled with the body 40 of the tibial augment 20 for rotation about an axis of rotation 86 extending longitudinally, in a second direction, by virtue of the engagement of the complementary helical threads 66 and 74.

Figure 4:
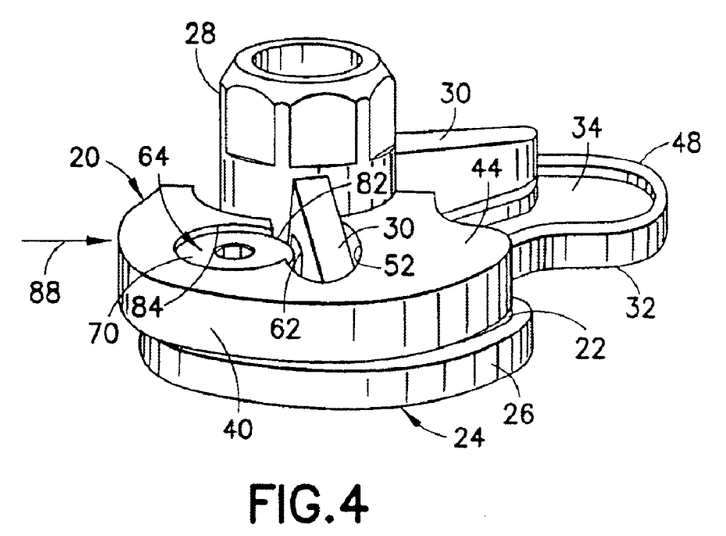
FIG. 4 is a perspective view taken from a distal aspect and showing the tibial augment being assembled with the tibial implant component.
Figure 5:
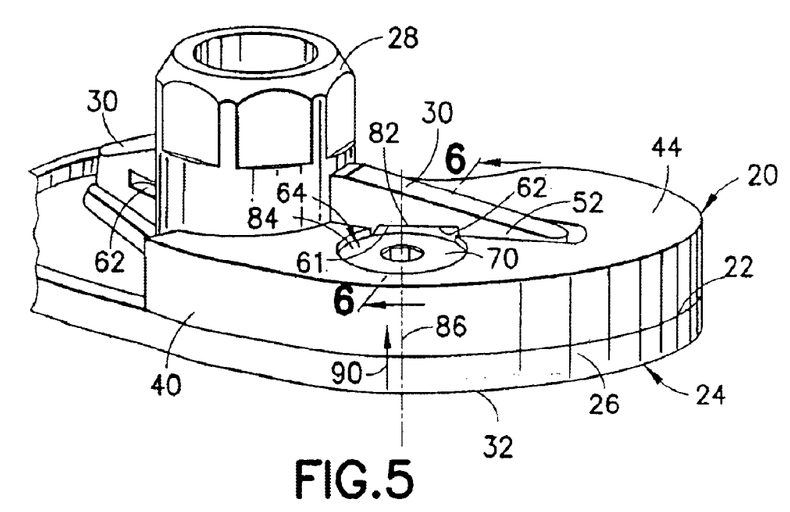
FIG. 5 is a perspective view showing the tibial augment in place at an augmentation location on the tibial implant component, and not yet secured in place.

When the selected tibial augment 20 is to be located and seated at the augmentation location 22, the tibial augment 20 is moved toward the augmentation location 22 by juxtaposing the tibial augment 20 with the tibial tray 26, with the tibial augment 20 slightly anterior of the augmentation location 22, as illustrated in FIG. 4. The keel 30 extends through the opening 52, and the head 70, with the threaded member 64 in the unlocked position, is juxtaposed with the slot 62 in the keel 30, with the portion 82 of the head 70 confronting slot 62. The tibial augment 20 then is moved in a posterior direction 88 so as to be seated appropriately at the augmentation location 22, as illustrated in FIG. 5. Upon such movement of the tibial augment 20 in the posterior direction, the portion 82 of head 70 moves transversely, in the first direction, and enters slot 62 so that when the tibial augment 20 is seated at the augmentation location 22, the portion 82 of head 70 lies within the slot 62, as shown in FIG. 6.

Figure 7:
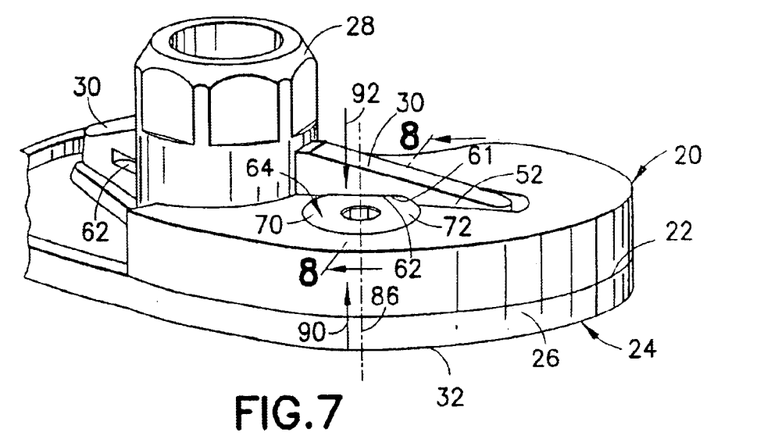
FIG. 7 is a perspective view showing the tibial augment in place at an augmentation location on the tibial implant component, and secured in place.
Figure 8:
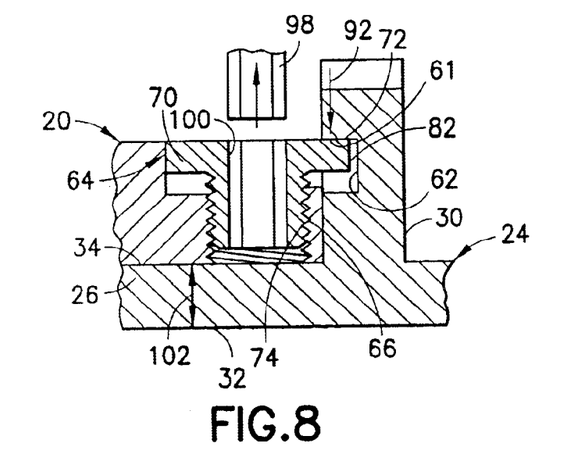
FIG. 8 is an enlarged fragmentary cross-sectional view taken along line 8—8 of FIG. 7.

Referring now to FIGS. 7 and 8, once seated at the augmentation location 22, as described above, tibial augment 20 is secured to tibial implant component 24 by the securing mechanism 60, as follows. The threaded member 64 is rotated about the axis of rotation 86 to move the head 70 distally in the second direction, indicated by arrow 90, into a second, or locking position shown in FIGS. 7 and 8. In the locking position, the locking surface 72 of head 70 is displaced longitudinally to be engaged with wall 61 of the slot 62 and to establish a locking force 92, aligned with the second direction, which urges the tibial augment 20 against the tibial tray 26 and thereby secures the tibial augment 20 to the tibial implant component 24, appropriately seated at the augmentation location 22. Rotation of the threaded member 64, and corresponding longitudinal displacement of locking surface 72, is accomplished merely by inserting a conventional drive wrench 98 into a drive socket 100 provided in the threaded member 64. The interengaged threads 66 and 74 assure that the locking force 92 is established readily and is maintained with sufficient magnitude to retain the tibial augment 20 in place for exemplary performance of the implanted tibial component 24.

Figure 6:
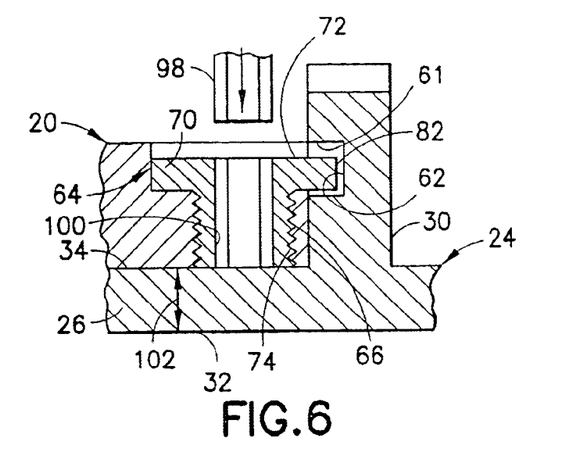
FIG. 6 is an enlarged fragmentary cross-sectional view taken along line 6—6 of FIG. 5.

As best seen in FIGS. 6 and 8, securing mechanism 60 accomplishes the securement of the tibial augment 20 on the tibial implant component 24 without disturbing the integrity of the proximal surface 32 of the tibial tray 26. Thus, as best seen in FIGS. 6 and 8, the maintenance of a longitudinal spacing 102 between the threaded member 64 and the proximal surface 32 of the tibial tray 26 assures that the proximal surface 32 remains unbroken. The full area of the proximal surface 32 remains available for the support of a bearing member, thereby maintaining a lower level of stress in the bearing material during service.

Further, no path is opened for migration of any particulate polyethylene which otherwise might emanate from the bearing material.

The tibial augment 20 advantageously is delivered from the factory with the threaded member 64 in place within the body 40, so that no assembly is required in the operating room. The implant procedure is facilitated by requiring the surgeon merely to select the appropriate tibial augment 20, seat the selected tibial augment 20 in place at the augmentation location 22, and then secure the seated tibial augment 20 in place with a simple wrenching operation.

Figure 9:
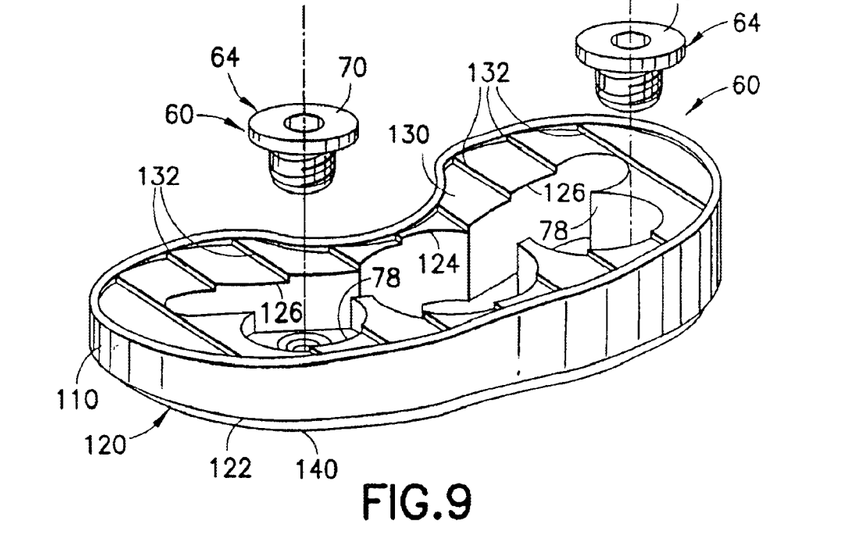
FIG. 9 is an exploded perspective view of component parts of another tibial augment constructed in accordance with the invention, taken from a distal aspect.
Figure 10:
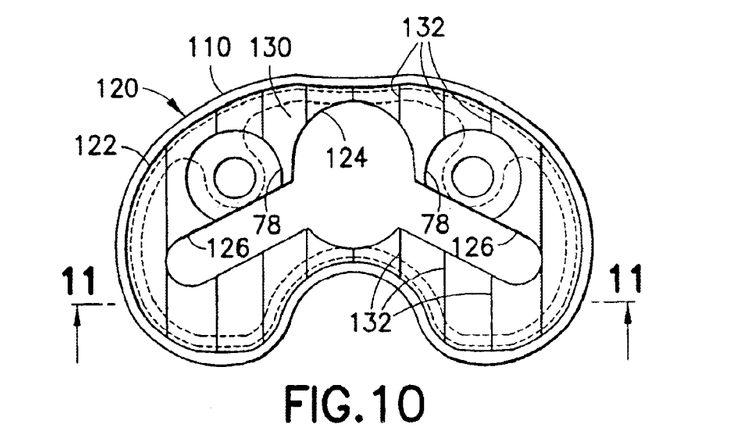
FIG. 10 is a plan view of a component part of FIG. 9.
Figure 11:
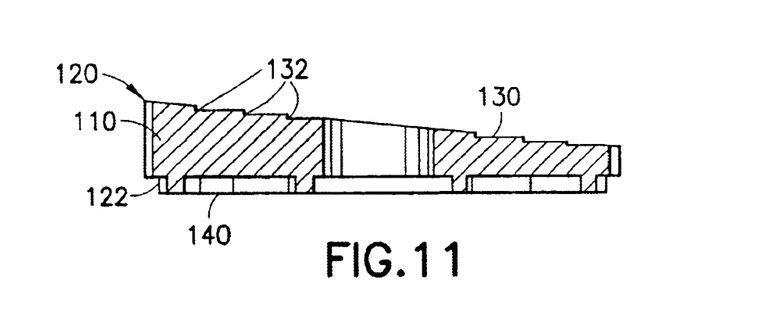
FIG. 11 is a cross-sectional view taken along line 11—11 of FIG. 10.

Turning now to FIGS. 9 through 11, as well as to FIG. 1, another embodiment of the present improvement is illustrated in an alternate body 110 of a tibial augment 120. In the present embodiment, the tibial augment 120 is to extend along the entire distal surface 34 of the tibial tray 26 of tibial implant component 24, rather than merely along a portion of the distal surface 34, as described in connection with the embodiment illustrated by tibial augment 20 above. Thus, the outer peripheral undercut 122 of the tibial augment 120 essentially follows the full peripheral rim 48 of the tibial tray 26, while an inner peripheral edge 124 follows a generally circular pattern for providing clearance for the stem boss 28, and somewhat rectangular openings 126 provide clearance for respective keels 30. Tibial augment 120 is secured in place upon tibial implant component 24 in essentially the same manner as described above in connection with tibial augment 20. A pair of securing mechanisms 60 are placed in the tibial augment 120, each securing mechanism 60 including a threaded member 64 having a head 70 to be located in a counterbore 78 for establishing a locking force, in concert with a corresponding slot 62, as described above in connection with tibial augment 20.

In order to enhance the performance of tibial augment 120, distal surface 130 of tibial augment 120 is provided with a surface configuration which includes "normalized"

surface portions. That is, surface portions 132 extend across the distal surface 130 in anterior-posterior directions and are oriented along the longitudinal direction, essentially normal to medial-lateral directions. In this manner, any tendency toward medial-lateral movements of the distal surface 130 relative to the confronting natural bone, during service, will be resisted by bone ingrowth along the distal surface 130.

The thickness of the tibial augment 120, that is, the distance between distal surface 130 and proximal surface 140 of the tibial augment 120, is shown to be varied along the medial-lateral direction in order to compensate for conditions encountered at an implant site. Tibial augments having different amounts of such a variation are made available for selection by a surgeon, interoperatively, so as to provide appropriate compensation for particular conditions observed by the surgeon at the implant site.

It will be apparent that the present improvement attains the several objects and advantages summarized above, namely: Enables a surgeon quickly and effectively to attach a selected augment to an implant component, such as the attachment of a selected tibial augment to a tibial implant component, interoperatively, without resorting to cementing and clamping, as described above, and without the necessity for assembling loose fasteners with the augment and the implant component; avoids deleterious effects which otherwise could result from migrating particulate polyethylene, as described above, as well as cold flow of polyethylene due to excessive stress at surfaces where the bearing member of a tibial implant is supported by the tibial tray of a tibial implant component; provides a self-contained augment in which a securement mechanism is assembled in the factory as a part of the augment for ready use by a surgeon without the necessity for further assembly of augment component parts during the implant procedure; simplifies the selection and placement of an appropriate augment at an implant site without undue delay, thereby benefitting the recipient of a prosthetic implant, as well as assisting the surgeon; provides a simple and highly effective securement arrangement for securing an augment, such as a tibial augment to a tibial implant component without the necessity for special instruments, tools or unusual skills; promotes accuracy and effectiveness in completing a prosthetic implant procedure; enhances the performance and longevity of a prosthetic knee implant which requires the use of a tibial augment; provides a relatively rugged implant assembly capable of exemplary performance over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement for facilitating securement of a selected tibial augment at an augmentation location on a tibial implant component, the tibial implant component having a tibial tray adjacent the augmentation location and a depending structure extending longitudinally from the tibial tray, the tibial tray having a proximal surface and an opposite distal surface, the improvement comprising:

an abutment on the depending structure, the abutment extending transversely along the depending structure adjacent the augmentation location;

a securing element coupled with the tibial augment for selective rotation about a longitudinal axis of rotation located adjacent the abutment when the tibial augment is placed at the augmentation location and juxtaposed with the tibial tray; and a securing surface on the securing element arranged for longitudinal displacement relative to the abutment upon rotation of the securing element, the longitudinal displacement engaging the securing surface with the abutment to establish a longitudinal securing force between the securing element and the depending structure for urging the tibial augment against the tibial implant component, and thereby secure the tibial augment to the tibial implant component at the augmentation location.

2. The improvement of claim 1 wherein the tibial augment includes a proximal surface for confronting the distal surface of the tibial tray when the tibial augment is placed at the augmentation location such that the securing force urges the proximal surface of the tibial augment against the distal surface of the tibial tray.

3. The improvement of claim 2 wherein the securing element is spaced longitudinally from the proximal surface of the tibial tray when the tibial augment is secured to the tibial implant component, at the augmentation location, such that the proximal surface of the tibial tray remains unbroken by the securing element.

4. The improvement of claim 2 wherein the confronting distal surface of the tibial tray and proximal surface of the tibial augment include complementary interengaging surface configurations for interlocking upon securement of the tibial augment to the tibial implant component, at the augmentation location.

5. The improvement of claim 1 wherein the securing element comprises a threaded member having a helical thread coupling the securing element with the tibial augment for movement in longitudinal directions relative to the tibial augment in response to rotation of the threaded member about the axis of rotation.

6. The improvement of claim 5 wherein the abutment comprises a wall of a slot extending transversely into the depending structure, and the threaded member includes a head for extending laterally into the slot when the tibial augment is located at the augmentation location, the securing surface being located on the head.

7. The improvement of claim 1 wherein the tibial augment includes a distal surface having surface portions extending across the distal surface in anterior-posterior directions and oriented essentially normal to medial-lateral directions.

8. The improvement of claim 1 wherein:

the abutment is one of more than one abutment in the depending structure, each abutment extending transversely along the depending structure adjacent the augmentation location;

the securing element is one of more than one securing element, each securing element being coupled with the tibial augment for selective rotation about a longitudinal axis of rotation located adjacent a corresponding abutment when the tibial augment is placed at the augmentation location and juxtaposed with the tibial tray; and the securing surface is one of more than one securing surface, each securing surface being located on a corresponding securing element arranged for longitudinal displacement relative to a corresponding abutment upon rotation of the corresponding securing element, the longitudinal displacement engaging the corresponding securing surface with the corresponding abutment to establish longitudinal securing forces between the securing elements and the depending structure for urging the tibial augment against the tibial implant component, and thereby secure the tibial augment to the tibial implant component at the augmentation location.

9. The improvement of claim 8 wherein the tibial augment includes a proximal surface for confronting the distal surface of the tibial tray when the tibial augment is placed at the augmentation location such that the securing forces urge the proximal surface of the tibial augment against the distal surface of the tibial tray.

10. The improvement of claim 9 wherein each securing element is spaced longitudinally from the proximal surface of the tibial tray when the tibial augment is secured to the tibial implant component, at the augmentation location, such that the proximal surface of the tibial tray remains unbroken by the securing elements.

11. The improvement of claim 9 wherein the confronting distal surface of the tibial tray and proximal surface of the tibial augment include complementary interengaging surface configurations for interlocking upon securement of the tibial augment to the tibial implant component, at the augmentation location.

12. The improvement of claim 8 wherein each securing element comprises a threaded member having a helical thread coupling the securing element with the tibial augment for movement in longitudinal directions relative to the tibial augment in response to rotation of the threaded member about the axis of rotation.

13. The improvement of claim 12 wherein each abutment comprises a wall of a slot extending transversely into the depending structure, and each threaded member includes a head for extending laterally into a corresponding slot when the tibial augment is located at the augmentation location, each securing surface being located on a corresponding head.

14. The improvement of claim 8 wherein the tibial augment includes a distal surface having surface portions extending across the distal surface in anterior-posterior directions and oriented essentially normal to medial-lateral directions.

15. A method for facilitating selective securement of a tibial augment at an augmentation location on a tibial implant component, the tibial implant component having a tibial tray adjacent the augmentation location and a depending structure extending longitudinally from the tibial tray, the tibial tray having a proximal surface and an opposite distal surface, the method comprising:

providing an abutment on the depending structure, the abutment extending transversely along the depending structure adjacent the augmentation location;

coupling a securing element with the tibial augment for selective rotation about a longitudinal axis of rotation located adjacent the abutment when the tibial augment is placed at the augmentation location and juxtaposed with the tibial tray;

providing a securing surface on the securing element; and rotating the securing element to displace the securing surface longitudinally relative to the abutment, the longitudinal displacement engaging the securing surface with the abutment to establish a longitudinal securing force between the securing element and the depending structure for urging the tibial augment against the tibial implant component, and thereby secure the tibial augment to the tibial implant component at the augmentation location.

16. The method of claim 15 including providing the tibial augment with a proximal surface for confronting the distal surface of the tibial tray when the tibial augment is placed at the augmentation location such that upon establishing the securing force, the securing force urges the proximal surface of the tibial augment against the distal surface of the tibial tray.

17. The method of claim 15 wherein the securing element is provided in the form of a threaded member having a helical thread coupling the securing element with the tibial augment such that upon rotation of the threaded member about the axis of rotation, the securing element is moved in longitudinal directions relative to the tibial augment.

18. The method of claim 15 including maintaining a longitudinal spacing between the securing element and the proximal surface of the tibial tray when the tibial augment is secured to the tibial implant component, at the augmentation location, such that the proximal surface of the tibial tray remains unbroken by the securing element.

19. An improvement for facilitating securement of a selected augment at an augmentation location on a prosthetic implant component, the improvement comprising:

an augment body;

an abutment on one of the augment body and the prosthetic implant component, the abutment extending in a first direction along the one of the augment body and the prosthetic implant component, adjacent the augmentation location;

a securing element coupled with the other of the augment body and the prosthetic implant component for selective rotation about an axis of rotation extending in a second direction transverse to the first direction and located adjacent the abutment when the augment is placed at the augmentation location and juxtaposed with the prosthetic implant component; and a securing surface on the securing element arranged for displacement in the second direction, relative to the augment body, upon rotation of the securing element about the axis of rotation, the displacement engaging the securing surface with the abutment to establish a securing force in the second direction, between the securing element and the abutment, for urging the augment against the prosthetic implant component, and thereby secure the augment to the prosthetic implant component at the augmentation location.

20. The improvement of claim 19 wherein the abutment is located on the prosthetic implant component and the securing element comprises a threaded member having a helical thread coupling the securing element with the augment body for movement in the second direction relative to the augment body in response to rotation of the threaded member about the axis of rotation.

21. The improvement of claim 20 wherein the abutment comprises a wall of a slot extending in the first direction into the prosthetic implant component, and the threaded member includes a head for extending in the first direction into the slot when the augment is located at the augmentation location, the securing surface being located on the head.

22. The improvement of claim 19 wherein the augment body includes a distal surface having surface portions extending across the distal surface in anterior-posterior directions and oriented essentially normal to medial-lateral directions.

23. A method for facilitating securement of a selected augment at an augmentation location on a prosthetic implant component, the method comprising:

providing an abutment on one of the augment and the prosthetic implant component, the abutment extending in a first direction along the one of the augment and the prosthetic implant component, adjacent the augmentation location;

coupling a securing element with the other of the augment and the prosthetic implant component for selective rotation about an axis of rotation extending in a second direction transverse to the first direction and located adjacent the abutment when the augment is placed at the augmentation location and juxtaposed with the prosthetic implant component; and rotating a securing surface on the securing element to displace the securing surface in the second direction, relative to the augment, upon rotation of the securing element about the axis of rotation, the displacement engaging the securing surface with the abutment to establish a securing force in the second direction, between the securing element and the abutment, for urging the augment against the prosthetic implant component, and thereby secure the augment to the prosthetic implant component at the augmentation location.

24. The method of claim 23 wherein the securing element is provided in the form of a threaded member having a helical thread coupling the securing element with the augment such that upon rotation of the threaded member about the axis of rotation, the securing element is moved in the second direction relative to the augment.

* * * * *